(12) United States Patent
Tsuchiya et al.

(10) Patent No.: US 8,357,904 B2
(45) Date of Patent: Jan. 22, 2013

(54) RADIATION IMAGING APPARATUS

(75) Inventors: Katsutoshi Tsuchiya, Hitachi (JP);
Takafumi Ishitsu, Hitachi (JP);
Tsuneaki Kawaguchi, Kashiwa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/061,857

(22) PCT Filed: Feb. 18, 2009

(86) PCT No.: PCT/JP2009/052759
§ 371 (c)(1),
(2), (4) Date: Mar. 2, 2011

(87) PCT Pub. No.: WO2010/026785
PCT Pub. Date: Mar. 11, 2010

(65) Prior Publication Data
US 2011/0164728 A1    Jul. 7, 2011

(30) Foreign Application Priority Data
Sep. 3, 2008   (JP) .................................. 2008-226311

(51) Int. Cl.
*G01T 1/161* (2006.01)
(52) U.S. Cl. ................................................. 250/363.02
(58) Field of Classification Search ... 250/363.01–363.1
See application file for complete search history.

(56) References Cited

U.S. PATENT DOCUMENTS

| | | | |
|---|---|---|---|
| 4,836,671 A * | 6/1989 | Bautista | 356/3.1 |
| 6,873,867 B2 | 3/2005 | Vilsmeier | |
| 7,141,812 B2 * | 11/2006 | Appleby et al. | 250/505.1 |
| 2005/0119560 A1 | 6/2005 | Mostafavi | |

FOREIGN PATENT DOCUMENTS

| | | |
|---|---|---|
| JP | 5-307082 A | 11/1993 |
| JP | 2001-324569 A | 11/2001 |
| JP | 2005-532532 A | 10/2005 |
| JP | 2006-81590 A | 3/2006 |

* cited by examiner

*Primary Examiner* — Kiho Kim
(74) *Attorney, Agent, or Firm* — Mattingly & Malur, PC

(57) ABSTRACT

A radiation imaging apparatus comprises display means for displaying an image obtained by imaging an object and light projection means for projecting a light projection mark onto the object, and displays a light projection position on the object onto which the light projection mark is projected on the image. The light projection mark is projected as a line of intersection which is perpendicular to the surface of a detector and at which two planar flat light beams visually intersect each other, and the light projection position on the image is moved according to the movements of the flat light beams. By calculating projected lines obtained by projecting the light projection lines projected onto the object by the flat light beams onto the surface and displaying the projected lines on the image, the light projection position is displayed as a point of intersection of the projected lines on the image.

9 Claims, 16 Drawing Sheets

INCIDENT SURFACE

RADIATION IMAGING APPARATUS

TECHNICAL FIELD

The present invention relates a radiation imaging apparatus including display means for displaying an image obtained by imaging an object to be imaged (subject).

BACKGROUND ART

A gamma camera, a SPECT (Single Photon Emission Computed Tomography) apparatus, a PET (Positron Emission Tomography) apparatus and the like are used as radiation imaging apparatuses. According to the radiation imaging apparatus, accumulation distribution of a radioactive pharmaceutical administered into the body of a subject can be known as an image, which is functional image information. Merging thereof with morphologic image information of an X-ray CT (Computed Tomography) or an MRI (Magnetic Resonance Imaging) superimposes the functional image information such as of a tumor and the morphologic image information. This allows reliable determination of existence of a tumor or the like and precise identification of a position thereof. However, apparatuses capable of such merging are large in size and capable of imaging only in a dedicated examination room. Accordingly, these apparatuses are suitable for a detailed examination, but unsuitable for frequent use on a treatment site such as an operating room.

On the other hand, it is attempted to easily grasp an internal RI accumulating position and identifies an incision site using a small gamma camera (e.g., see Patent Literature 1) on a treatment site, such as sentinel lymph node biopsy in a breast cancer operation using RI (Radio Isotope) procedure.
PATENT LITERATURE 1: JP-A-2001-324569

DISCLOSURE OF INVENTION

Technical Problem

A radiation imaging apparatus including an X-ray CT or an MRI is capable of obtaining where a tumor or the like resides in the subject, as an image. However, in order to actually identify an incision site on the body surface of the subject, the obtained image and the subject are compared with each other.

A small gamma camera is capable of bringing a detector of the small gamma camera close to subject. Accordingly, a high resolution image (the functional image information) can be obtained. However, it is only roughly identified which position on the body surface of the subject the position indicating an RI accumulating point on the obtained image corresponds to, from a positional relationship between the subject and the detector and a position indicating the RI accumulating point on an image.

It is thus an object of the present invention to provide a radiation imaging apparatus capable of clearly indicating where on the body surface of a subject the position on the image resides.

Solution to Problem

In order to attain the object, characteristics of the present invention reside in a radiation imaging apparatus including: display means for displaying an image obtained by imaging an object to be imaged; and light projection means provided in a detector detecting a radiation incident from the object to be imaged for projecting a light projection mark on the object to be imaged, wherein a light projection position on the object to be imaged onto which the light projection mark is projected is displayed on the image, and the light projection means is operated from an opposite side to an incident surface on which the radiation is incident in the detector in accordance with the light projection position displayed on the image, and the light projection position on the object to be imaged is moved.

Advantageous Effects of Invention

The present invention can provide a radiation imaging apparatus capable of clearly indicating where on the body surface of a subject the position on the image resides.

Another object, feature and advantage of the present invention will become apparent from the following description of embodiments of the present invention pertaining to accompanying drawings.

Figure 1A:
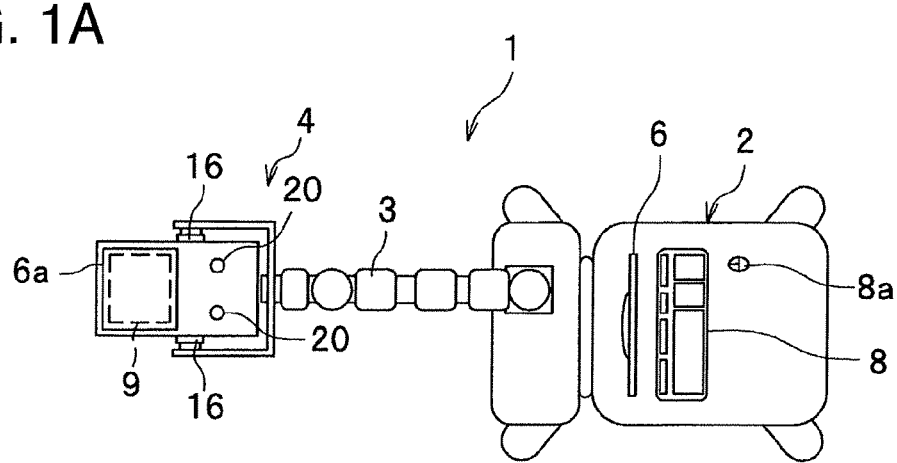
FIG. 1A is a plan view of a radiation imaging apparatus (gamma camera) according to a first embodiment of the present invention.

REFERENCE SIGNS LIST 1 radiation imaging apparatus (gamma camera, SPECT apparatus)
2 main body of the apparatus (including a power source and a data processing apparatus)
3 arm
4 detector
5 processing PC
6, 6a display means (monitor)
7 image
8 keyboard
8a mouse
9 imaging field
10 bed
11a, 11b wide-angle laser marker
12a, 12b planar flat light beam (laser light beam)
13a, 13b projected line (on the imaging field)
14a, 14b positional coordinates for an image of a wide-angle laser marker
15 marker moving means
16 vertical moving means (slide mechanism)
17 LED
18 slit
19 turning mechanism
19a turning knob
20 light projection means
21 radiation detection means
21a (semiconductor radiation) detection element
22 collimator
23 detector substrate
24 FPGA
25 integrated circuit (ASIC)
26 detector container (inner container)
27 inner container holder
28 casing (outer container)
29 light, gamma-ray and electromagnetic shield
30 object to be imaged (subject)
31a, 31b light projection line
32 SLN (sentinel lymph node)
33 RI injection site
34a, 34b projected line (on an image)
41 laser marker
42 minor
43 guide advancing mechanism
44 turning mechanism
45 light projection position (projected point)
46 (laser) light beam
50 line of intersection
51a point of intersection (light projection position) of projected lines (on the surface of detector)
51b point of intersection (light projection mark, light projection position) of light projection lines (on the body surface)
51c point of intersection (light projection position) of projected lines (on an image)
52 gantry
53 RI accumulation
54 image of an object to be imaged (subject)

BEST MODE FOR CARRYING OUT THE INVENTION

Next, embodiments of the present invention will be described in detail with appropriate reference to drawings. Note that elements common to the drawings are assigned with the same symbols and redundant description thereof is omitted.

First Embodiment

Figure 1B:
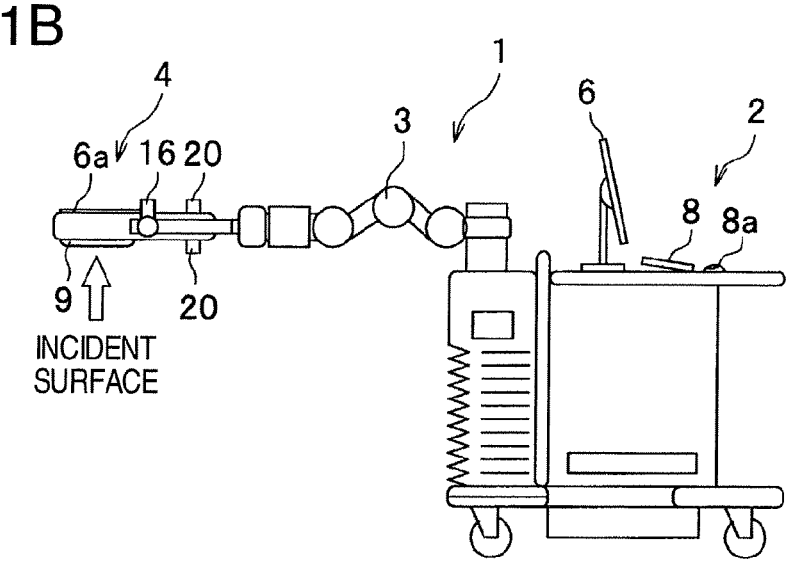
FIG. 1B is a side view of the radiation imaging apparatus (gamma camera) according to the first embodiment of the present invention.
Figure 1C:
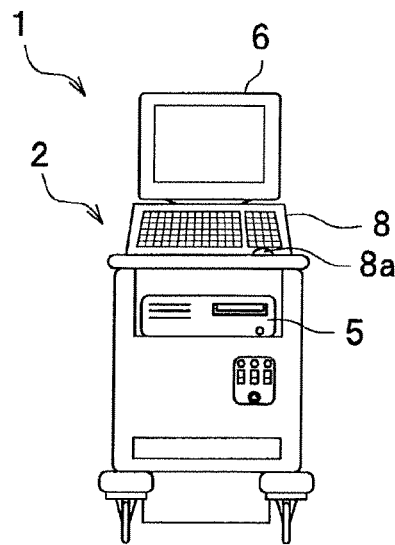
FIG. 1C is a front view of the radiation imaging apparatus (gamma camera) according to the first embodiment of the present invention.

FIGS. 1A to 1C show plan, side and front views of a radiation imaging apparatus (gamma camera) 1 according to a first embodiment of the present invention, respectively. FIGS. 1A to 1C show a pixel-type gamma camera as the radiation imaging apparatus 1.

As shown in FIGS. 1A to 1C, the radiation imaging apparatus 1 includes: a main body 2 of the apparatus including a power source and a data processing apparatus (not shown); an arm 3 having a multiple degree-of-freedom including up and down, back and forth, right and left, and swinging; a detector 4 attached to the distal end of the arm 3; and display means (monitor) 6 for displaying an image obtained by imaging an object to be imaged. The main body 2 of the apparatus includes: a processing PC 5 (see FIG. 1C); and input means, such as a keyboard 8 and a mouse 8a, for inputting the light projection position of a light projection mark, which will be described later. The processing PC 5, which may include the data processing apparatus, controls generation and display of image information displayed by the display means 6. The details of the control will be described in detail with respect to a marking method, which will be described later.

As shown in FIG. 1B, the detector 4 includes: an imaging field 9 provided on the incident surface on which radiation is incident; display means 6a provided on an opposite side to the incident surface and for displaying an image obtained by imaging the object to be imaged as with the display means 6; vertical moving means 16 provided on a side of the incident surface for moving the detector 4 in a direction perpendicular to the incident surface; and light projection means 20 for projecting a light projection mark onto the object to be imaged.

The radiation imaging apparatus (gamma camera) 1 shown in FIGS. 1A to 1C is a mobile apparatus movable by means of wheels, and capable of being brought into not only a nuclear medical examination room but also an operating room, a hospital room and the like. The arm 3 can bring the detector 4 close to a subject in a free angle to whom a radioactive pharmaceutical has been administered. This enables RI accumulation distribution in the body to be displayed on display means 6 and 6a as a high resolution image. More specifically, the display means 6a arranges an image to be displayed on the display means 6a so as to be congruent, or identical in size and shape, with that on the imaging field 9 and in a superimposed manner in a view perpendicular to the incident surface, and thus superimposes a site with invisible RI accumulation distribution and an image displaying RI accumulation distribution. This allows an operator to easily understand positional relationship of the RI accumulation distribution at the site as if to watch the RI accumulation distribution directly at the site.

Figure 2A:
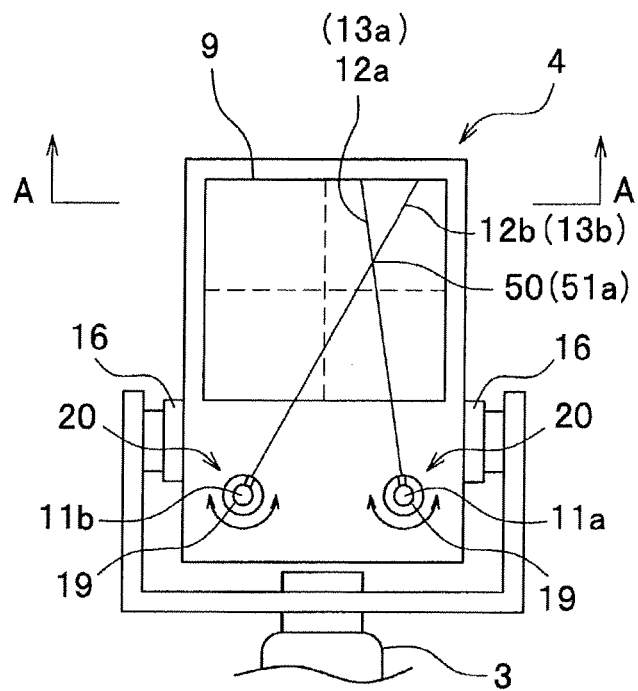
FIG. 2A is a plan view of a detector of the radiation imaging apparatus (gamma camera) according to the first embodiment of the present invention.

FIG. 2A is a diagram showing the detector 4 viewed from a side of the incident surface. The light projection means 20 are disposed at two positions separated from each other. One piece of the light projection means 20 includes: a wide-angle laser marker 11a emitting a planar flat light beam 12a that is visually planer and perpendicular to the incident surface; and a turning mechanism 19 that turns the wide-angle laser marker 11a about a turning axis perpendicular to the incident surface. Another piece of light projection means 20 also includes: a wide-angle laser marker 11b emitting a planar flat light beam 12b that is visually planer and perpendicular to the incident surface; and a turning mechanism 19 that turns the wide-angle laser marker 11b about a turning axis perpendicular to the incident surface. The operator can recognize that a light projection mark resides on a line of intersection 50 on which the planar flat light beams 12a and 12b intersect with each other. The two turning mechanisms 19 turn the respective wide-angle laser markers 11a and 11b, thereby moving the planar flat light beams 12a and 12b. This allows the line of intersection 50 and further the light projection mark to be moved. The line of intersection 50 is always kept perpendicular to the incident surface. The wide-angle laser markers 11a and 11b are arranged on the same side as that of the imaging field 9 of the detector 4. The wide-angle laser markers 11a and 11b are arranged outside of the imaging field 9 in order to project the planar flat light beams 12a and 12b perpendicular to a plane defined by the imaging field 9, and attached at a position where the planar flat light beams 12a and 12b intersect but do not overlapped with each other on the imaging field 9. The two turning mechanisms 19 for turning the respective laser markers 11a and 11b turn independently from each other. The turning angles of the respective laser markers 11a and 11b are fed back to the data processing apparatus of the main body 2 of the apparatus (see FIGS. 1A to 1C) by means of potentiometers and the like (not shown) in the turning mechanisms 19. The data processing apparatus is thus capable of controlling the respective turning angles of the laser markers 11a and 11b. Projected lines 13a and 13b (see FIG. 3) drawn on the imaging field 9 by the planar flat light beams 12a and 12b on the basis of the turning angles measured by the potentiometers and the like embedded in the turning mechanisms 19 are displayed as projected lines 34a and 34b (see FIGS. 4 and 6) on an image 7 (see FIGS. 4 and 5) displayed by the display means 6 and 6a (see FIGS. 1A and 1C).

Figure 2B:
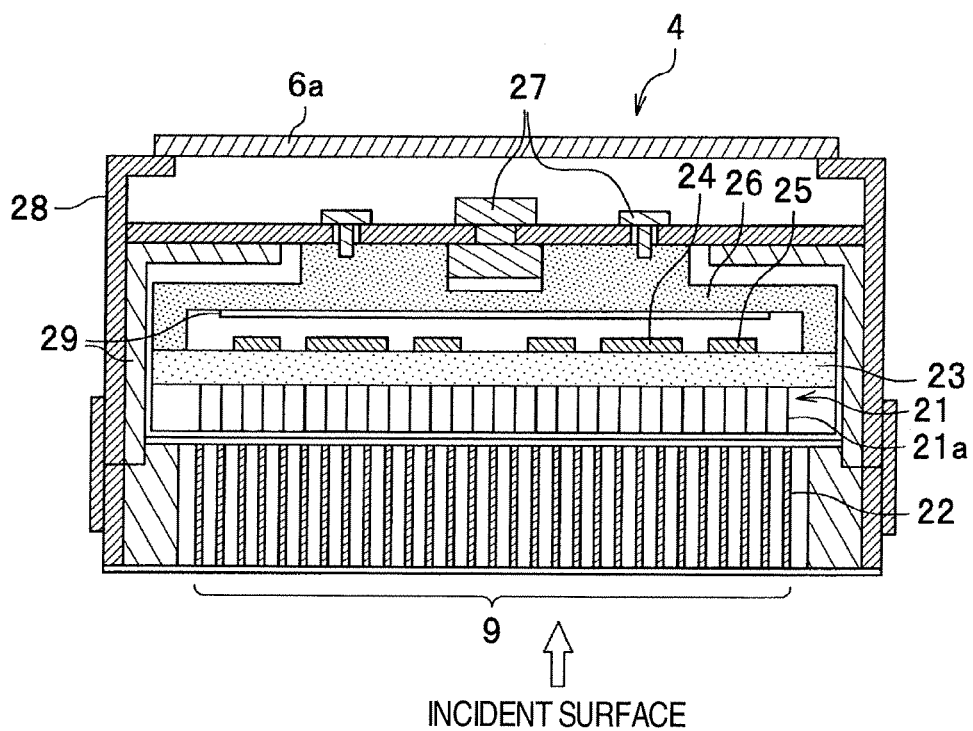
FIG. 2B is a sectional view taken along the line A-A of FIG. 2A.

FIG. 2B shows a sectional view taken along the line A-A of FIG. 2A in an enlarged manner. The detector 4 is embedded with a collimator 22 and radiation detection means 21 including a multiplicity of (radiation) detection elements 21a.

The collimator 22, which includes a plurality of pores made of lead or the like, limits the incident direction of radiation incident onto the detection elements 21a to a direction perpendicular to the surface (the incident surface; see FIG. 1B), and passes only gamma-rays along a certain direction among radiation (gamma-rays) emitted from the body of object to be imaged (subject), thereby selecting the gamma-rays incident on the surface (incident surface) of the collimator 22. The gamma-rays having passed through the collimator 22 are detected by the multiplicity of detection elements 21a arranged in a planar manner (two-dimensionally) on the detector substrate 23. The radiation detection means 21 arranges the multiplicity of detection elements 21a for detecting gamma-rays from the object to be imaged having passed through the collimator 22 and incident thereon in a grid pattern.

The detector substrate 23 is mounted on its back surface with an integrated circuit (ASIC) 25 and an FPGA (Field Programmable Gate Allay) 24 for signal-processing a gamma-rays detection signal from the detection elements 21a. The gamma-rays detection signal is counted by the ASIC 25 and the FPGA 24 via the detector substrate 23. The count value thereof and the detection time are measured. The digital information thereof and ID information (pixel position information) of the detection element 21a having detected the gamma-rays are output to the data processing apparatus of the main body 2 of the apparatus (see FIGS. 1A to 1C). The digital information is accumulated with respect to each pixel (detection element 21a), and a (gamma-rays-projected) image 7 (see FIG. 5) in a direction perpendicular to the detector 4 (the incident surface) is generated. This image is displayed on the display means 6 and 6a (see FIGS. 1A to 1C). The positional relationship between the plurality of detection elements 21a and a plurality of pixels configuring the image 7 are preliminarily in association with each other as the ID information.

The displayed image 7 (see FIG. 4) is a (gamma-rays-projected) image viewed from the incident surface in a direction perpendicular to the incident surface. As described above, the line of intersection 50 (see FIG. 2A) is also perpendicular to the incident surface. Accordingly, the lines of intersection 50 and the pixels (detection elements 21a) of the image correspond to each other in a one-to-one correspondence. The light projection mark is generated on the line of intersection 50. Accordingly, the light projection marks and the pixels (detection elements 21a) correspond to each other in a one-to-one correspondence. Thus, if one position of the light projection mark is determined, the corresponding pixel (detection elements 21a) of the image is also determined. Conversely, if one pixel (detection elements 21a) of the image is determined, the position of the corresponding light projection mark is also determined. That is, the position of the light projection mark can be designated on the image 7.

The detector substrate 23 is supported by a detector container 26. The detector container 26 is supported by the inner container holder 27 to the casing 28. The collimator 22 and the detector substrate 23 are covered by a shield 29 and a casing 28 made of iron, lead or the like except for the incident surface (front face) of the collimator 22, and shielded from the light, gamma-rays and electromagnetic waves generated outside. The incident surface (front face) of the collimator 22 is covered with a metallic plate material, such as aluminum, through which gamma-rays easily pass, as an imaging field 9, and the side of the collimator 22 is shielded from the light and electromagnetic waves generated outside.

Figure 3:
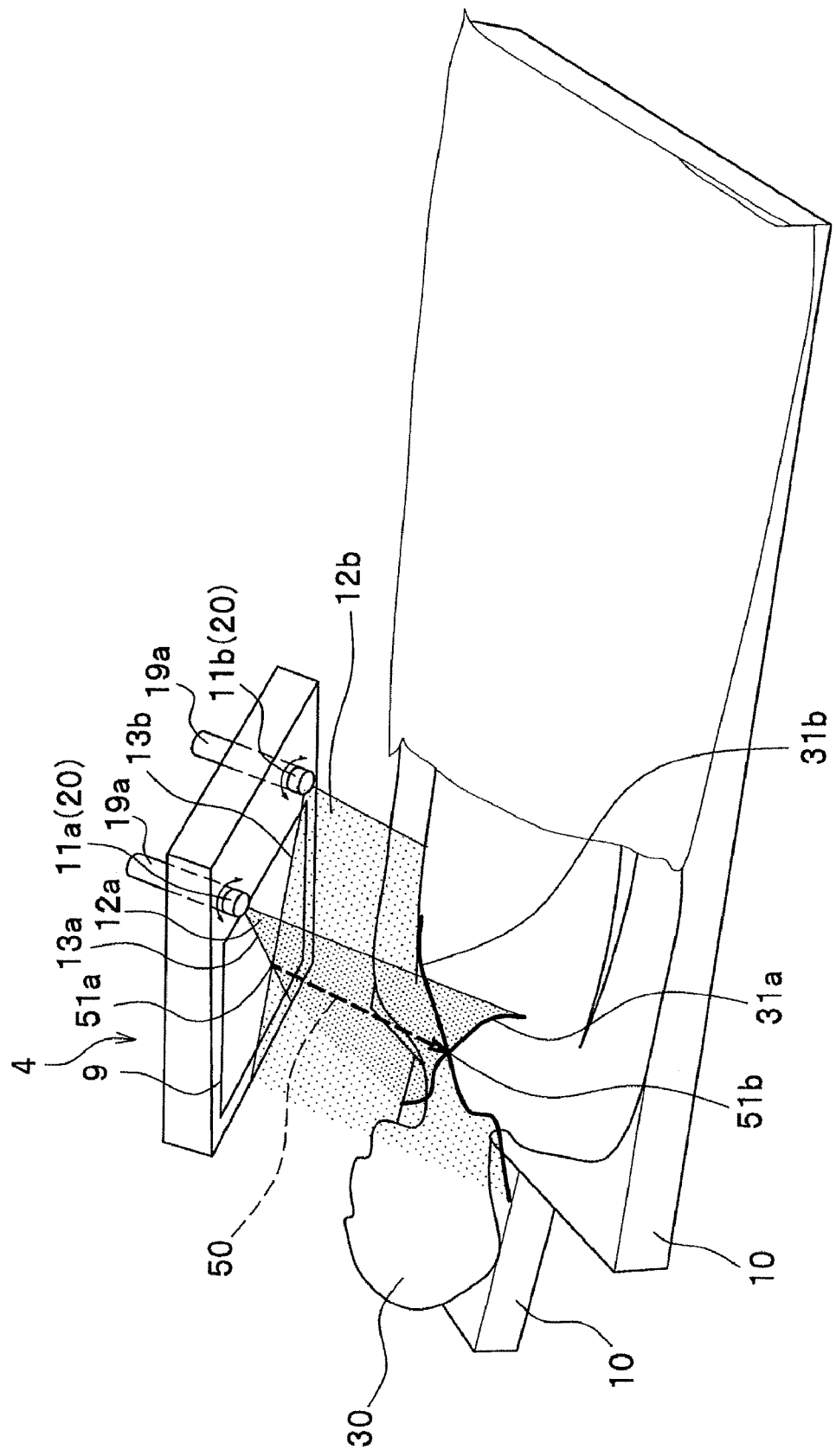
FIG. 3 is a diagram showing situations of marking by the radiation imaging apparatus (gamma camera) (No. 1)

FIG. 3 shows situations of light projection marking using the detector 4 of the radiation imaging apparatus (gamma camera) 1 viewed from a direction oblique to the object 30 to be imaged. The planar flat light beams 12a and 12b, which are laser light beam, are always projected perpendicularly from the imaging field 9. Accordingly, the line of intersection 50 of the two planar flat light beams 12a and 12b are perpendicular to the imaging field 9, and the line of intersection 50 and the extension line thereof pass the point of intersection 51a on the imaging field 9. The line of intersection 50 reaches the point of intersection 51b on the body surface. The position of the point of intersection 51b is the light projection position of the light projection mark. The point of intersection between the projected line 13a, which is the projection of planar flat light beam 12a on the imaging field 9, and the projected line 13b, which is the projection of planar flat light beam 12b on the imaging field 9, is the point of intersection 51a. The point of intersection between a light projection line 31a, which is projection of the planar flat light beam 12a on the object 30 to be imaged, and a light projection line 31b, which is projection of the planar flat light beam 12b on the object 30 to be imaged is the point of intersection 51b, which is to be the light projection mark.

Turning knobs 19a may be provided in order to manually turn the wide-angle laser markers 11a and 11b, which will be described later in detail. The turning knobs 19a are arranged on a side opposite to the imaging field 9 of the detector 4, which is a side of the display means 6a (see FIG. 1B). Accordingly, the operator can turn the wide-angle laser markers 11a and 11b while watching the taken image 7 (see FIG. 4) displayed on the display means 6a.

Figure 4:
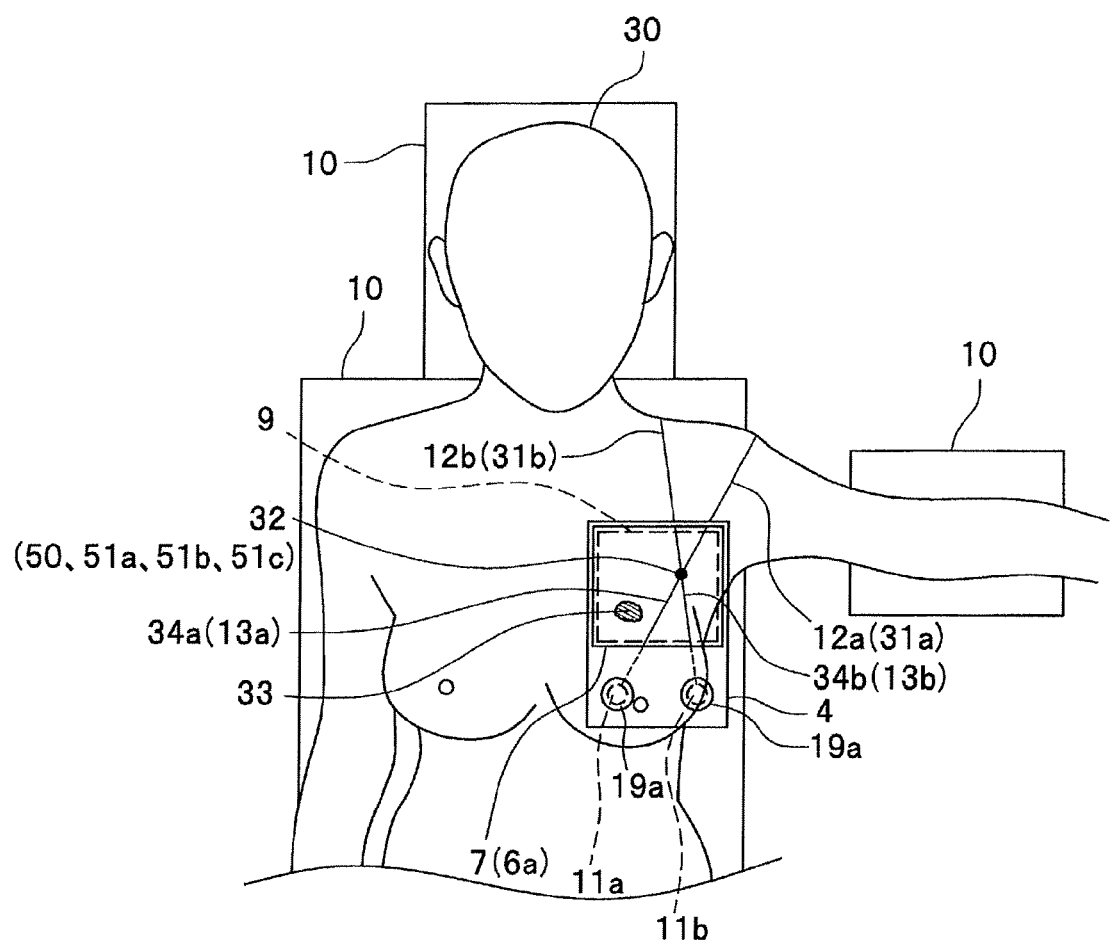
FIG. 4 is a diagram showing situations of marking by the radiation imaging apparatus (gamma camera) (No. 2)
Figure 5:
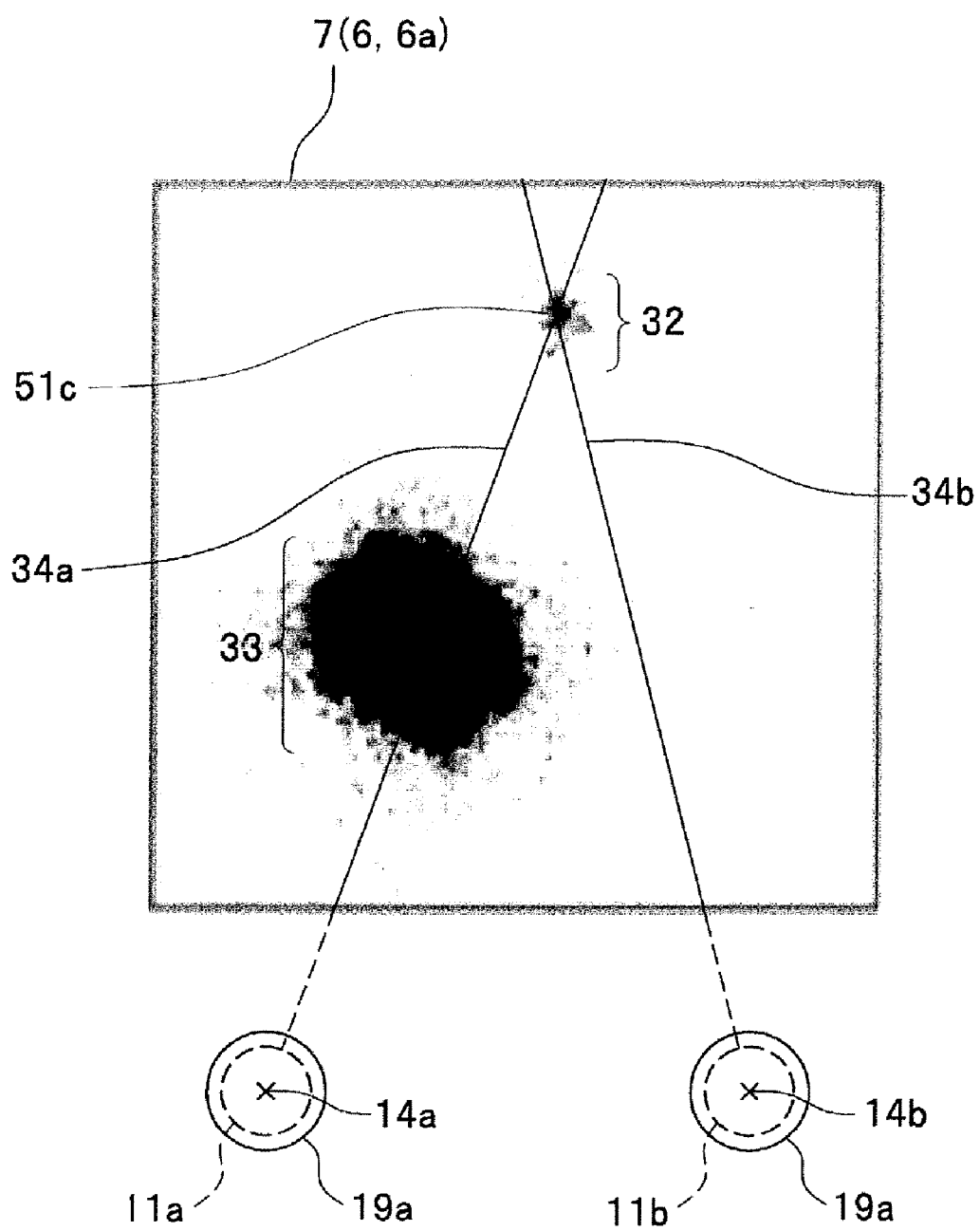
FIG. 5 is a diagram showing a light projection position on an object to be imaged, onto which a light projection mark is projected, on a taken image in a superimposed manner.

FIG. 4 shows situations of light projection marking using the detector 4 of the radiation imaging apparatus (gamma camera) 1 viewed from a front surface of the object 30 to be imaged. FIG. 5 is an enlarged diagram around the display means 6a of the detector 4 of FIG. 4, and showing the light projection position on the object to be imaged, onto which a light projection mark is projected, as the point of intersection 51c on the taken image 7 in a superimposed manner. These diagrams show an example where the present invention is applied to sentinel lymph node biopsy in a breast cancer operation, which will be described later.

As shown in FIG. 4, the side of the imaging field 9 of the detector 4 is close and opposite to the object 30 to be imaged. The side of the display means 6a of the detector 4 faces the outside (upwardly from this sheet). The taken image 7 is displayed on the display means 6a. The planar flat light beams 12a and 12b are projected from the respective wide-angle laser markers 11a and 11b toward the body surface of the object 30 to be imaged. The planar flat light beams 12a and 12b generate the respective light projection lines 31a and 31b on the body surface of the object 30 to be imaged. The projected lines 13a and 13b are generated on the imaging field 9. In FIG. 4, the projected lines 13a and 13b are overlapped with the projected lines 34a and 34b displayed on the image 7, respectively.

On the other hand, as shown in FIGS. 4 and 5, for example an RI injection site 33 and an SLN (Sentinel Lymph Node) 32 are imaged on the image 7 displayed on the display means 6a. For example, in order to project the light projection mark on the SLN 32, for the sake of marking the SLN 32 on the body surface, the point of intersection 51c between the projected lines 34a and 34b displayed on the image 7 is disposed on the SLN 32 on the image 7. It is displayed such that the projected line 34a is resultantly passes on the SLN 32 in the image 7 and the extension line passes on the positional coordinates 14a of the wide-angle laser marker 11a with respect to the image 7. It is displayed such that the projected line 34b is resultantly passes on the SLN 32 in the image 7 and the extension line passes on the positional coordinates 14b of the wide-angle laser marker 11b with respect to the image 7.

As shown in FIG. 4, the light projection mark corresponds to the point of intersection 51b on the body surface of the object 30 to be imaged. The point of intersection 51b on the body surface corresponds to the point of intersection 51a on the imaging field 9 via the line of intersection 50. The point of intersection 51a on the imaging field 9 corresponds to the point of intersection 51c on the image 7. Accordingly, the point of intersection 51a on the imaging field 9, the point of intersection 51b on the body surface and the point of intersection 51c on the image 7 agree with each other; the positional relationships therebetween are in a one-to-one correspondence.

Conversely, if the operator (medical doctor) sets (designates) the light projection position of the point of intersection 51c agrees on any position on the image 7, for example on the position of the SLN 32, the point of intersection 51b to be the light projection mark can be projected on the light projection position on the body surface. The doctor can easily confirm the optimal incision site by marking the point of intersection 51b (on the body surface) with a pen or the like.

The doctor designates (double clicks) any position on the image 7, for example, the position of the SLN 32, thereby automatically turns the wide-angle laser markers 11a and 11b under control of the processing PC 5, and allows the planar flat light beams 12a and 12b to pass on a position on the body surface corresponding to the designated position, thus generating the point of intersection 51b to be the light projection mark. On the other hand, the projected lines 34a and 34b virtually corresponding to the projected lines 13a and 13b on the imaging field 9 by means of the planar flat light beams 12a and 12b are calculated and displayed on the image 7. Note that the wide-angle laser markers 11a and 11b may manually be operated to move the point of intersection 51c to any position. The details thereof will be described later.

Next, marking in biopsy of the SLN 32, so-called sentinel lymph node biopsy, will be described. Conventionally, in a breast cancer operation, a procedure (Halsted Mastectomy) largely removing surrounding tissue in addition to a primary focus has been conducted for preventing recurrence since long before. However, it has been known that, for example, radical dissection (extirpation) of a group of lymph nodes in the axilla, which is to be a metastatic pathway of a cancer, produces large side effects including occurrence of tense at the arm and pain in life after the operation. In order to reduce disability owing to dissection of lymph nodes, in recent years a method has been attempted that, based on a hypothesis that the site first to be metastasized from the cancer is a sentinel lymph node (SLN) 32 among numerous lymph nodes, identifies the SLN 32, determines presence and absence of metastasis by means of immediate biopsy (SLN B: Sentinel Lymph Node Biopsy) on the dissected SLN 32, and determines the procedure. If the SLN 32 is not metastatic, there is a significantly low possibility of metastasis to another site. Accordingly, another lymph node is not dissected, and only the primary focus is resected. If it is found that the SLN 32 is metastatic, the entire local lymph nodes having a possibility of metastasis are resected according to the Halsted Mastectomy as with the conventional cases.

Methods of identifying the SLN 32 for immediate biopsy include the RI method. A radioactive pharmaceutical (RI pharmaceutical) is hypodermically injected around the primary focus. The lymph nodes where the RI pharmaceutical has accumulated is searched for using a gamma probe or the like. It is determined that the lymph node the probe has first reached is the SLN 32. In the first embodiment, in order to obtain image information of the position of the SLN 32, the technique using a small gamma camera 1 is described as one example. More specifically, the doctor identifies an injection site 33 and the SLN 32 based on the taken image 7, and dissects the SLN 32. Correct identification of the position of the SLN 32 on the body surface allows the incision area to be minimized. To realize the minimization, it is required to correctly mark the position of the SLN 32 on the body surface.

Figure 6:
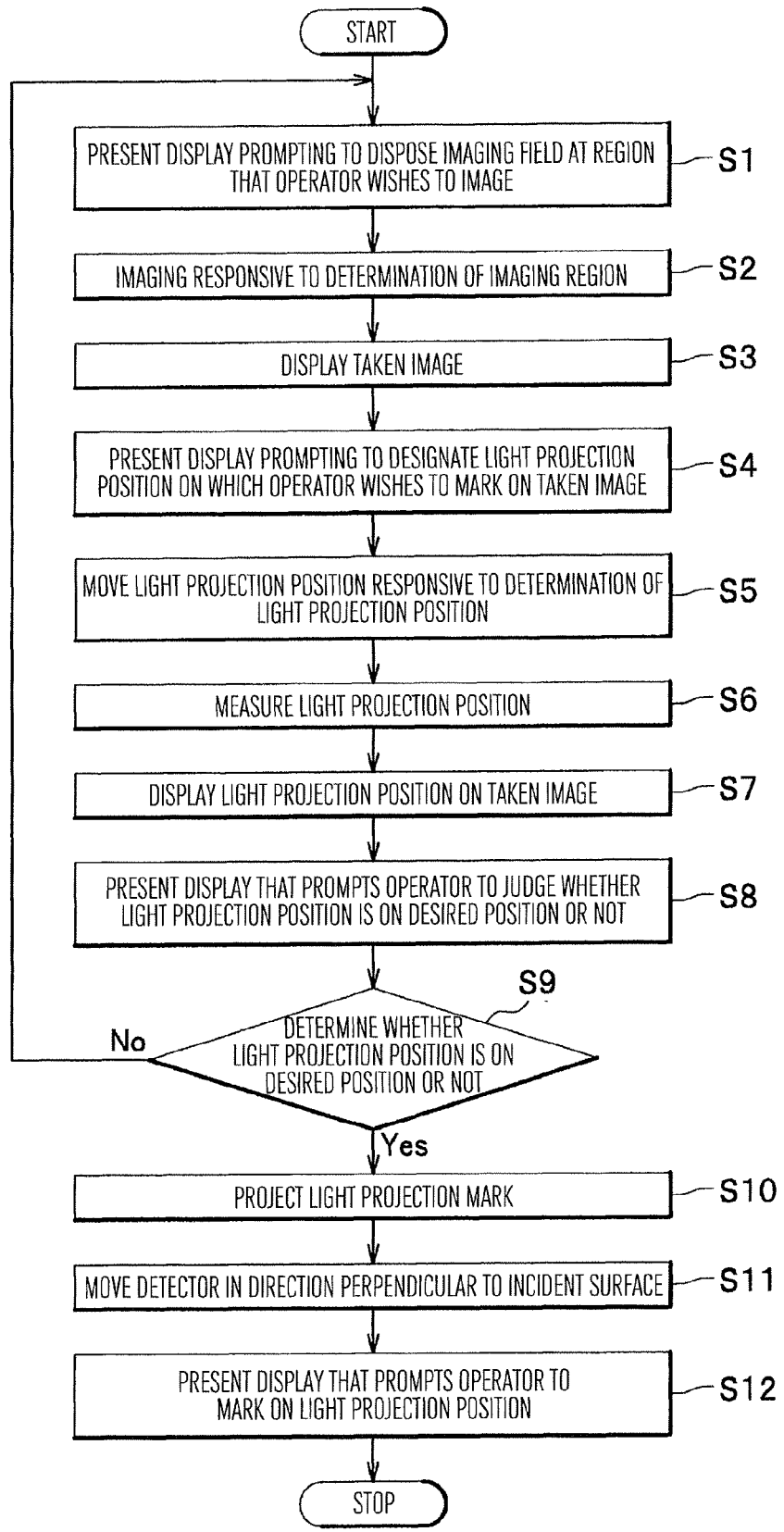
FIG. 6 is a flowchart of a marking method by means of radiation imaging apparatus (gamma camera) according to the first embodiment of the present invention.

FIG. 6 shows a flowchart of a marking method by means of radiation imaging apparatus (gamma camera) 1 according to the first embodiment of the present invention.

First, in step S1, the processing PC 5 (see FIG. 1C) of the gamma camera 1 presents a display prompting to dispose the imaging field 9 at a region that the operator wishes to image, on the display means 6 and 6a. The operator manually disposes the imaging field 9 at a region that the operator wishes to image according to the display, and inputs that an imaging region has been determined using input means, such as the mouse 8a.

In step S2, the processing PC 5 receives a determination of the imaging region, takes an image, and obtains the image 7 based thereon.

In step S3, the processing PC 5 displays the taken image 7 on the display means 6 and 6a.

In step S4, the processing PC 5 presents a display prompting to designate a marking position on which the operator wishes to mark on the taken image 7, on the display means 6 and 6a. The operator designates the marking position that he/she wishes to mark on the image 7 according to the display, and inputs that the marking position has been determined using the input means, such as the mouse 8a. The marking position may be designated using a GUI (graphical user interface), move a pointer generated on the image to a desired marking position using the mouse 8a or the like, and designate the position at the destination as the marking position by double-clicking.

In step S5, the processing PC 5 receives the marking position and the determination thereof, and, based thereon, moves the light projection position on the object 30 to be imaged onto which the light projection mark is projected. More specifically, the processing PC 5 calculates the respective angles of turning of the turning mechanisms 19 such that the planar flat light beams 12a and 12b pass the marking position, on the basis of the marking position. The processing PC 5 turns the turning mechanisms 19 such that the angles become the respective angles calculated, thereby allowing the light projection position to move to the marking position.

In step S6, the processing PC 5 equivalently measures the light projection position by causing the respective turning mechanisms 19 to measure the present turning angles.

In step S7, the processing PC 5 calculates the projected lines 13a and 13b along which the planar flat light beams 12a and 12b are projected on the imaging field 9 on the basis of the present turning angles, and calculates the position of the point of intersection 51a on which the projected lines 13a and 13b intersect with each other. The position of the point of intersection 51a is displayed on the display means 6 and 6a as the point of intersection 51c, or the present light projection position, superimposed on the taken image 7.

In step S8, the processing PC 5 presents a display that prompts the operator to judge whether the present light projection position is on a desired position or not, on the display means 6 and 6a. Based on this display, the operator refers to the taken image 7 where the present light projection position (point of intersection 51c) is displayed, judges whether the present light projection position is on the desired position or not, and inputs the judgment result using the input means, such as the mouse 8a.

In step S9, the processing PC 5 determines whether the present light projection position is on the desired position or not on the basis of the judgment result. If it is determined that the present light projection position is on the desired position (step S9, Yes), the processing proceeds to step S10. If it is determined that the present light projection position is not on the desired position (step S9, No), the processing returns to step S1 or may return to S4.

In step S10, the processing PC 5 switches on the wide-angle laser marker to actually generate planar flat light beams 12a and 12b, thereby irradiating the object to be imaged on the line of intersection 50 of the planar flat light beams 12a and 12b with the light projection mark. Although it is unnecessary to light the wide-angle laser marker before step S9, it has been described as if the wide-angle laser marker always light before step S9, for example before step S1, for the sake of easy understanding of operation of the gamma camera 1. As a matter of course, there is no problem that the wide-angle laser marker lights before step S9. If the marker lights, it can be confirmed that the gamma camera 1 normally operates.

Figure 7:
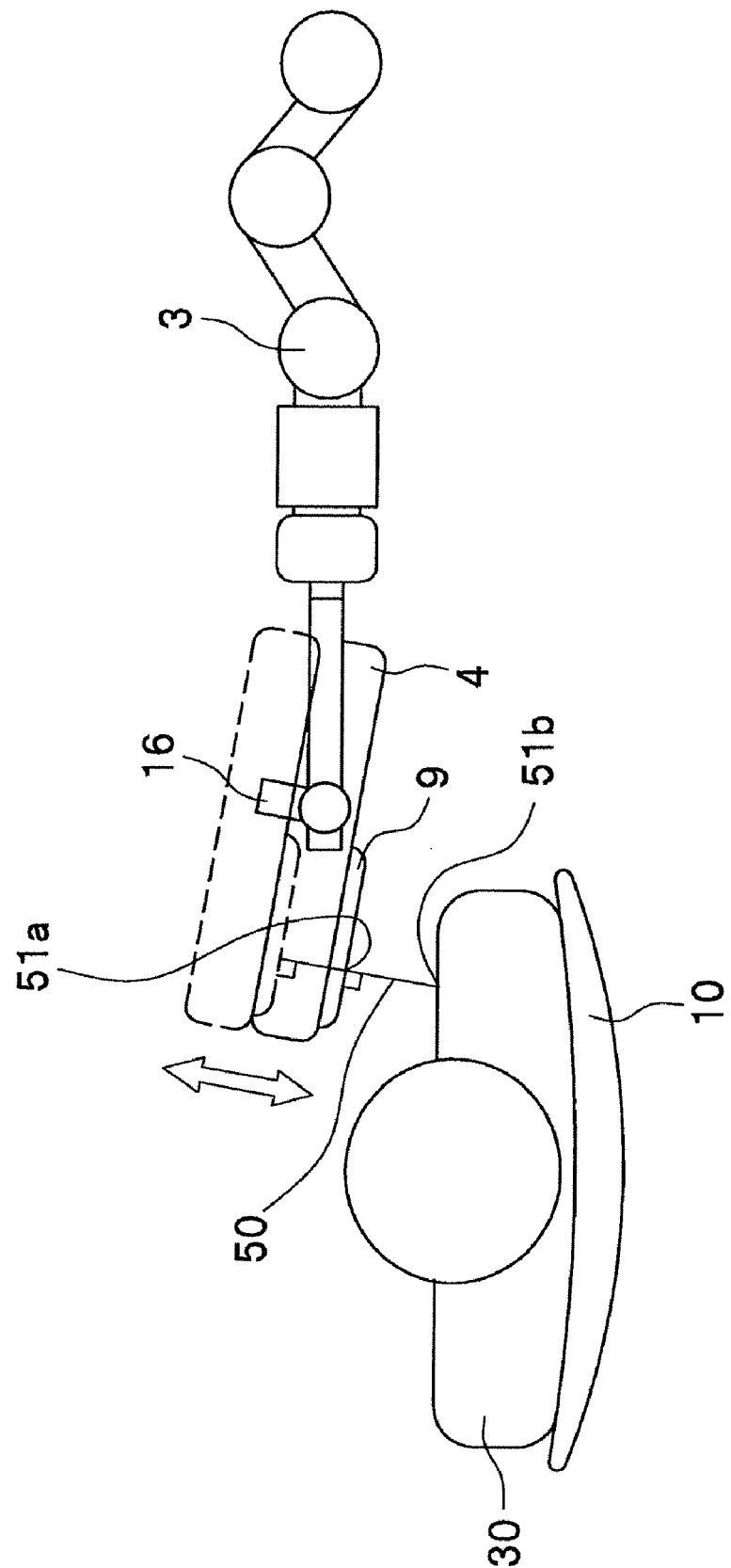
FIG. 7 is a diagram showing situations where the detector (collimator) is moved in a direction perpendicular to the surface of the detector (collimator) while a light projection mark (light projection position) is kept so as not to move in the marking method by means of the radiation imaging apparatus (gamma camera)

As shown in FIG. 7, in step S11, the processing PC 5 causes the vertical moving means 16 to move the detector 4 in the direction perpendicular to the incident surface. Before the movement, the detector 4 is close to the object to be imaged, which allows highly sensitive imaging. However, because of the closeness, the operator cannot insert the hand for marking between the detector 4 and the object to be imaged. This movement allows marking by the operator's hand. Since the point of intersection 51b (light projection position) on the body surface does not move before and after the movement, marking can be performed correctly.

In step S12, the processing PC 5 presents a display that prompts the operator to mark on the light projection position, on the display means 6 and 6a. According to this display, the operator marks on the light projection position on which the light projection mark is irradiated using a marker, such as a pen. This is the end of the marking method.

The marking in the first embodiment is applicable to not only a small portable gamma camera but also a typical stationary gamma camera. The description has been made using the display means 6a attached to the detector 4 as the display means, for the sake of simplicity of description. Without limitation thereto, the marking can also be performed using the display means 6 of the main body 2 of the apparatus instead of the display means 6a.

(Variation 1 of First Embodiment)

Figure 8:
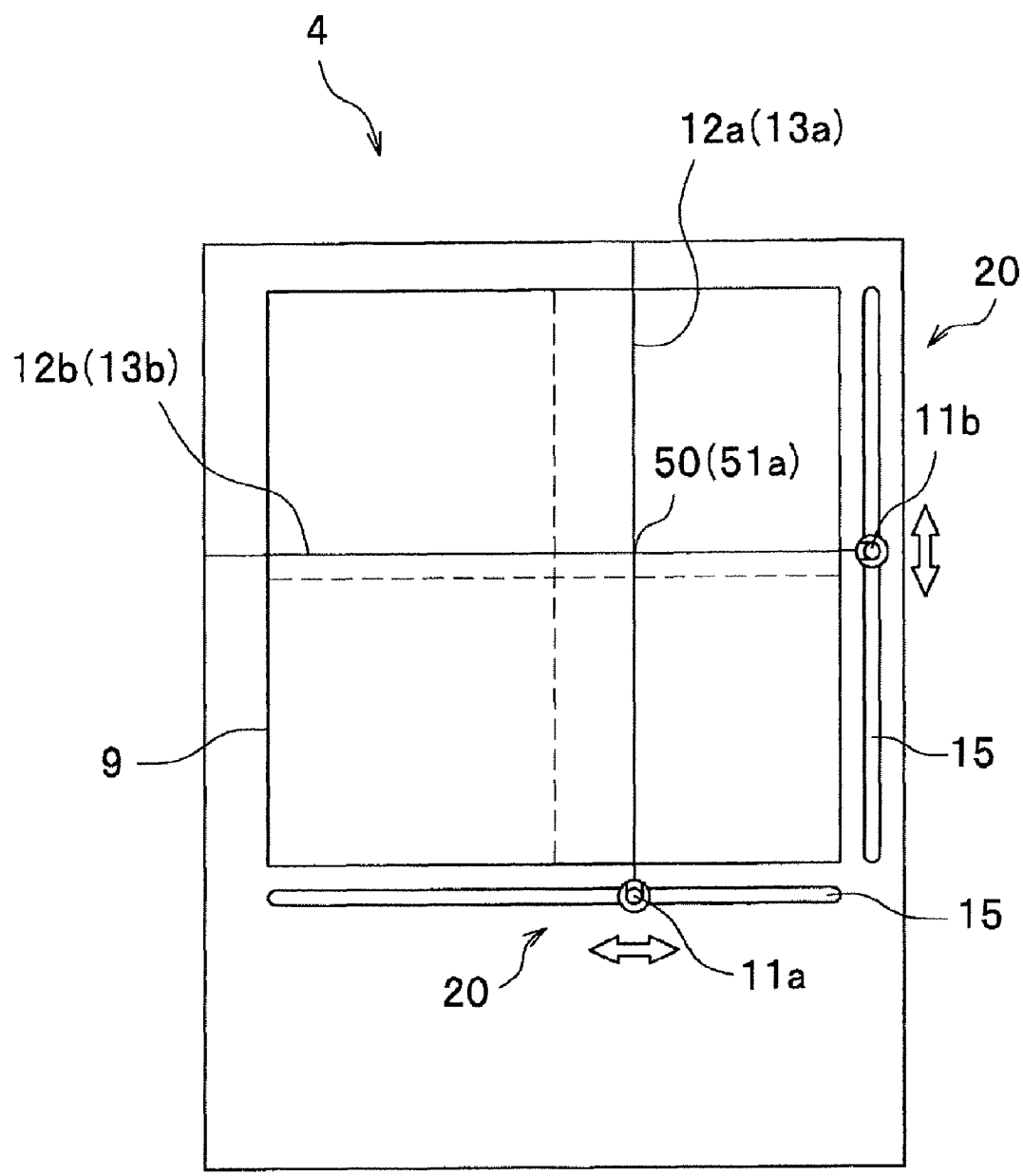
FIG. 8 is a plan view of a detector of a radiation imaging apparatus (gamma camera) according to a variation 1 of the first embodiment of the present invention.

FIG. 8 shows a plan view of a detector 4 of a radiation imaging apparatus (gamma camera) 1 according to a variation 1 of the first embodiment of the present invention. The variation 1 is different in the structure of the light projection means 20 from the first embodiment. In the first embodiment, the two wide-angle laser markers 11a and 11b are turned. In the variation 1, marker moving means 15 is provided along the vertical and horizontal sides of the imaging field 9, the wide-angle laser markers 11a and 11b are moved along the vertical and horizontal sides of the imaging field 9, thereby moving the line of intersection 50.

(Variation 2 of First Embodiment)

Figure 9:
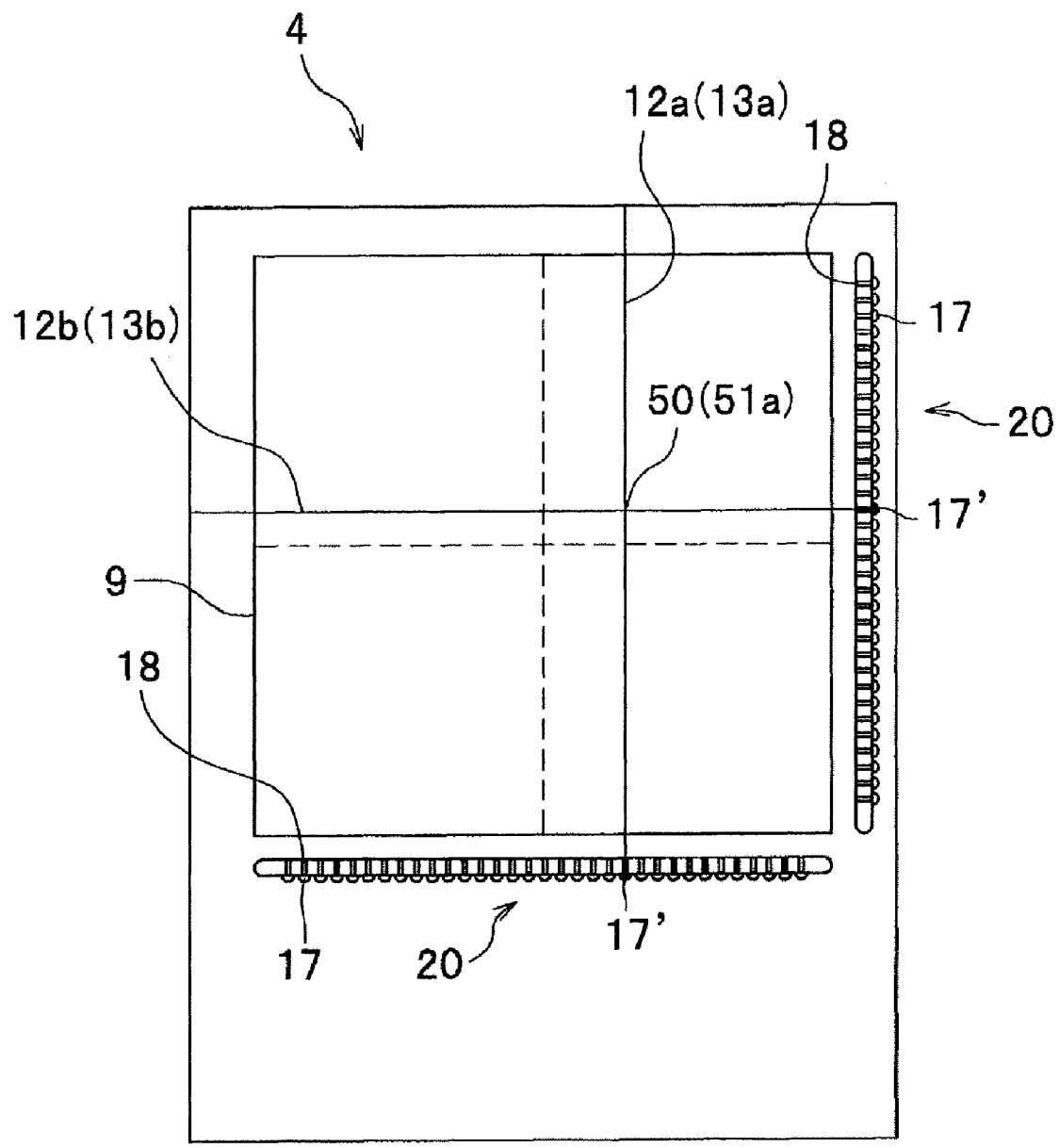
FIG. 9 is a plan view of a detector of a radiation imaging apparatus (gamma camera) according to a variation 2 of the first embodiment of the present invention.

FIG. 9 shows a plan view of a detector 4 of a radiation imaging apparatus (gamma camera) 1 according to a variation 2 of the first embodiment of the present invention. The variation 2 is also different in the structure of the light projection means 20 from the first embodiment. The variation 2 includes: a line of an array of LEDs 17 provided along each of vertical and horizontal sides of the imaging field 9; and slits 18 provided so as to be associated with respective LEDs 17 opening toward the imaging field 9 in a one-to-one correspondence. The vertically and horizontally arranged numbers of LEDs 17 agree with the numbers of lines and columns of arrays of the detection elements 21a (see FIG. 2B), respectively. The light emitted from the LEDs 17 passes the slits 18 and thus becomes the planar flat light beams 12a and 12b. The line of intersection 50 can be generated by lighting each one of vertical and horizontal LEDs 17 (LEDs 17'). The line of intersection 50 can be moved by changing the vertical and horizontal LEDs 17 to be lighted.

(Variation 3 of First Embodiment)

Figure 10:
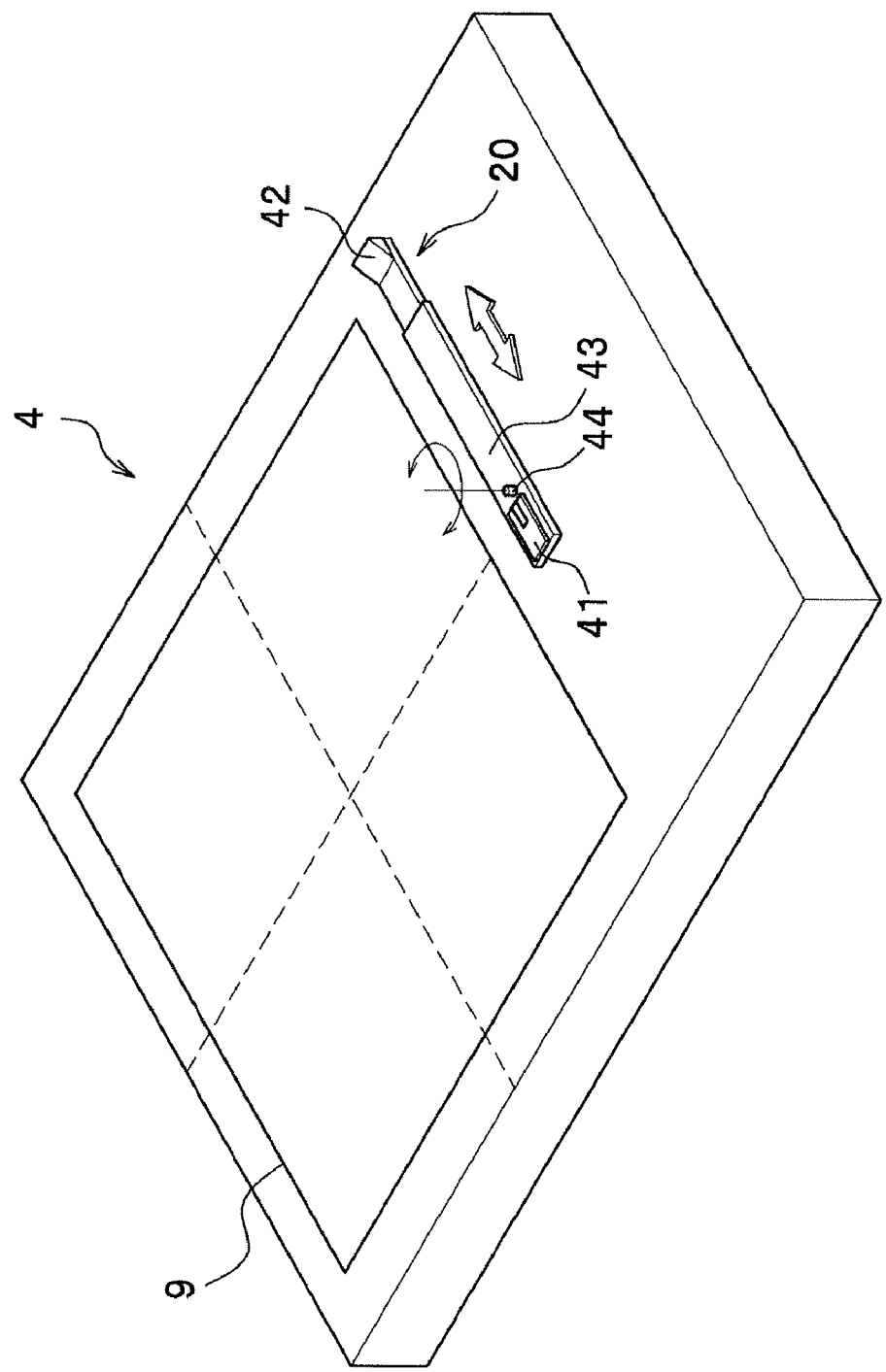
FIG. 10 is a perspective view of light projection means of a detector of a radiation imaging apparatus (gamma camera) according to a variation 3 of the first embodiment of the present invention when retracted.
Figure 11:
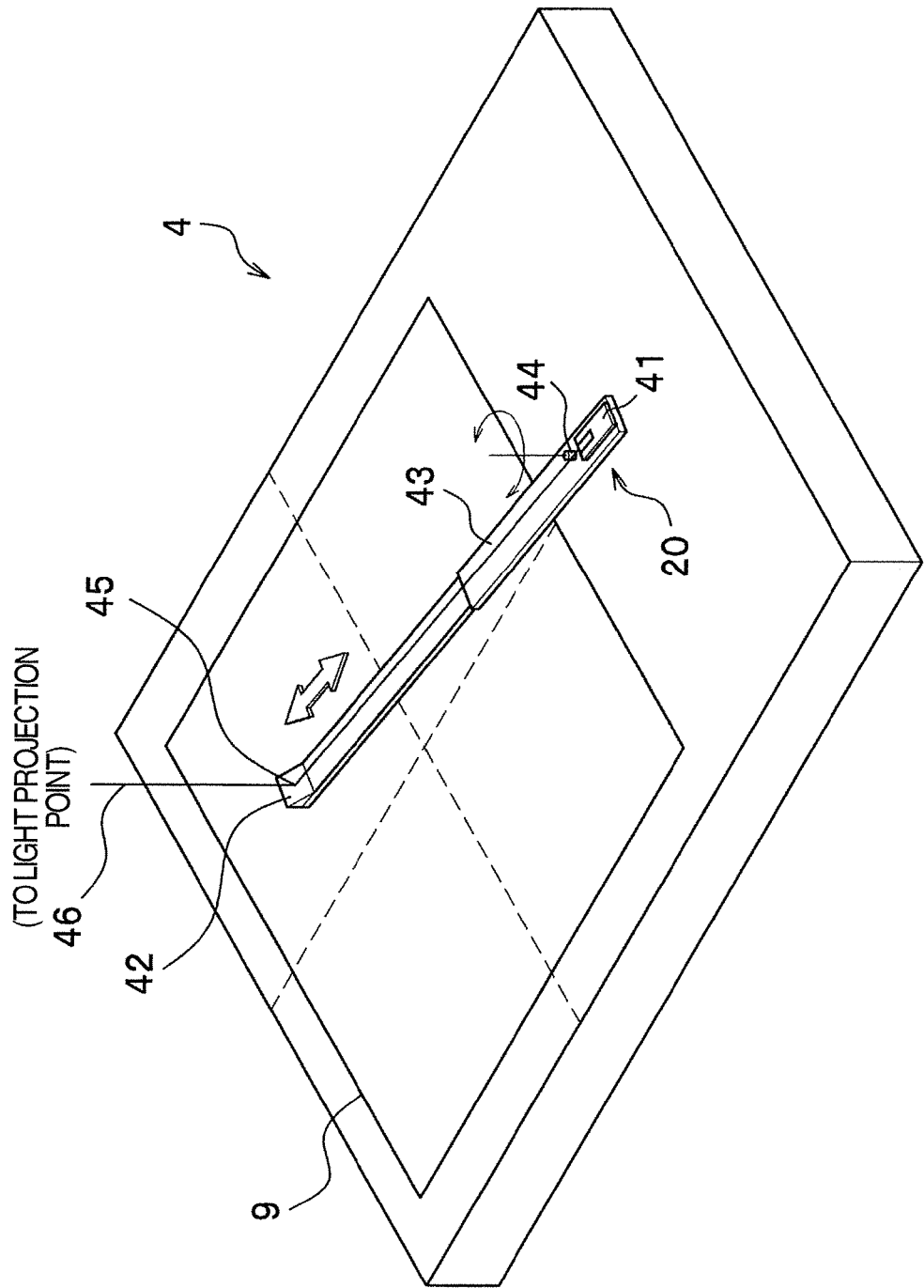
FIG. 11 is a perspective view of the detector of the radiation imaging apparatus (gamma camera) according to the variation 3 of the first embodiment of the present invention when marking is performed.

FIG. 10 shows a perspective view of light projection means 20 of a detector 4 of a radiation imaging apparatus (gamma camera) 1 according to a variation 3 of the first embodiment of the present invention when retracted. FIG. 11 shows a perspective view when marking is performed. The variation 3 is also different in the structure of the light projection means 20 from the first embodiment. The light projection means 20 includes: a laser marker 41 emitting a linear laser light beam 46; a mirror 42 reflecting the (laser) light beam 46 in a direction perpendicular to the incident surface of the imaging field 9; a guide advancing mechanism 43 capable of setting the distance between the laser marker 41 and the mirror 42 to a desired distance; and a turning mechanism 44 provided outside of the imaging field 9 and capable of turning the guide advancing mechanism 43 to set a desired angle.

The laser light beam 46 emitted from the laser marker 41 is reflected by the mirror 42, and advances in a direction perpendicular to the incident surface of the imaging field 9. The laser light beam 46 advancing in the direction perpendicular to the incident surface functions as the line of intersection 50 in the first embodiment. The point of intersection 51a (see FIG. 3) on the imaging field 9 in the first embodiment may be replaced with the light projection position (projected point) of the laser light beam 46 reflected by the minor 42. The point of intersection 51b (see FIG. 3) on the imaging field 9 in the first embodiment may be replaced with a light projection position on which the laser light beam 46 is projected on the body surface. Further, a projected point 45 (light projection position) on the image is generated instead of the point of intersection 51c on the image in the first embodiment. The generation method thereof is substantially identical to the generation method of the point of intersection 51c. Accordingly, the variation 3 also exerts advantageous effects analogous to those of the first embodiment. Further, in the variation 3, as shown in FIG. 10, the light projection means 20 are stored in a retracted position on imaging. As shown in FIG. 11, only on marking on the body surface, the position of the minor 42 is moved to a location corresponding to a designated position on the image 7 (see FIG. 5) and allows the vertical laser light beam 46 to be projected on any designated position.

(Variation 4 of First Embodiment)

Figure 12:
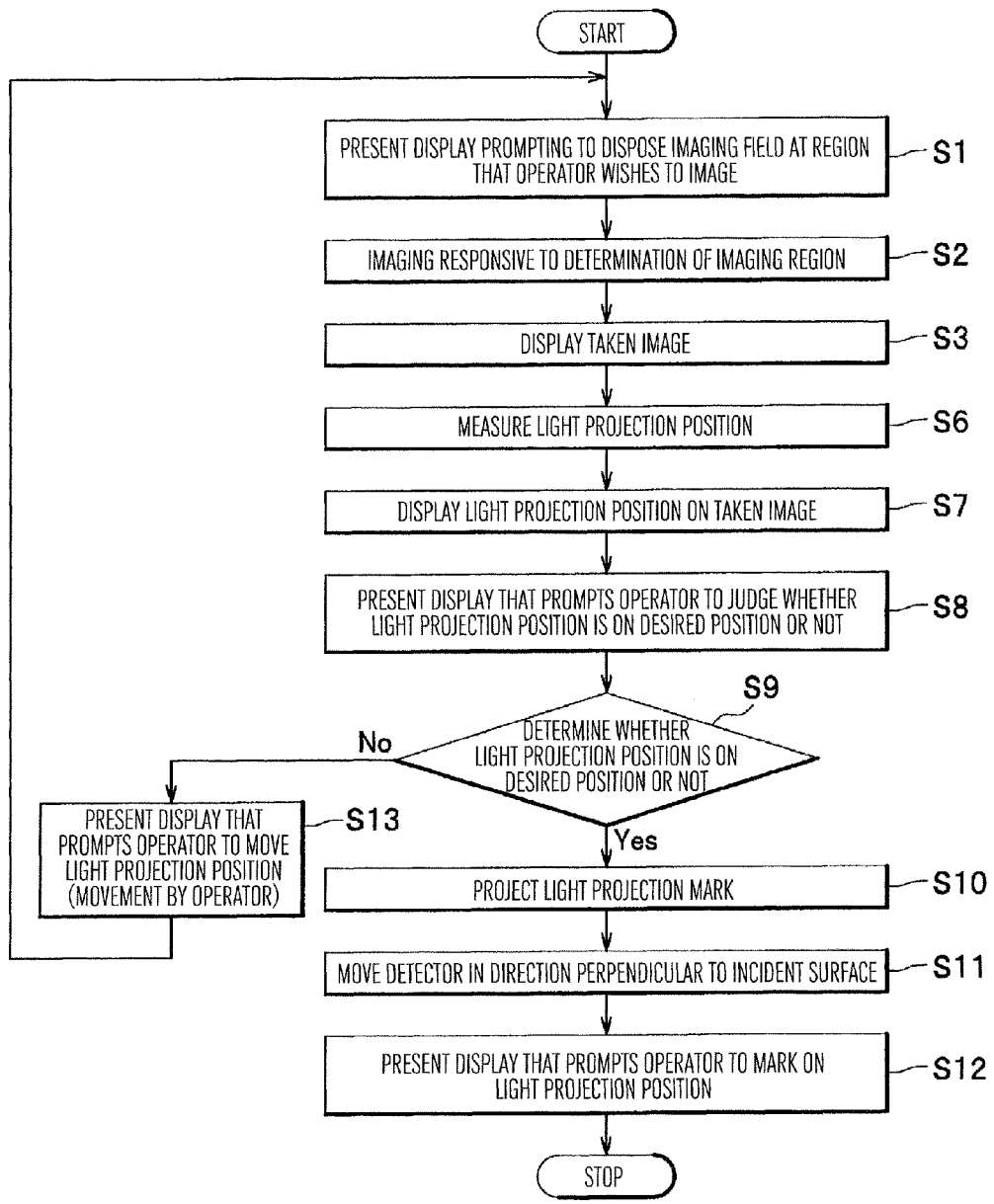
FIG. 12 is a flowchart of a marking method by means of a radiation imaging apparatus (gamma camera) according to a variation 4 of the first embodiment of the present invention.

FIG. 12 shows a flowchart of a marking method by means of a radiation imaging apparatus (gamma camera) 1 according to a variation 4 of the first embodiment of the present invention. The variation 4 is a case of manually turning the wide-angle laser markers 11a and 11b and so on. Accordingly, in comparison with the flowchart of FIG. 6, steps S4 and S5 thereof are omitted, and step S13 is added to the case of No in step S9.

In step S13, the processing PC 5 presents a display that prompts the operator to move the light projection position, on the display means 6 and 6a. Based on the display, the operator turns the turning knobs 19a (see FIG. 4) to turn the respective wide-angle laser markers 11a and 11b, thereby moving the light projection position. After the movement, the operator inputs that the movement has been completed using the input means, such as the mouse 8a. The processing returns to step S1 after the manual angle adjustment. Accordingly, the respective angles of the wide-angle laser markers 11a and 11b are measured for every manual turn (step S6), the light projection position is displayed on the image 7 again (step S7), and these processes are repeated until the light projection position is determined to agree with a desired position (step S9, Yes). The operation by the operator is only turning the turning knobs 19a. Accordingly, the adjustment does not require big efforts although it is made manually.

Second Embodiment

Figure 13:
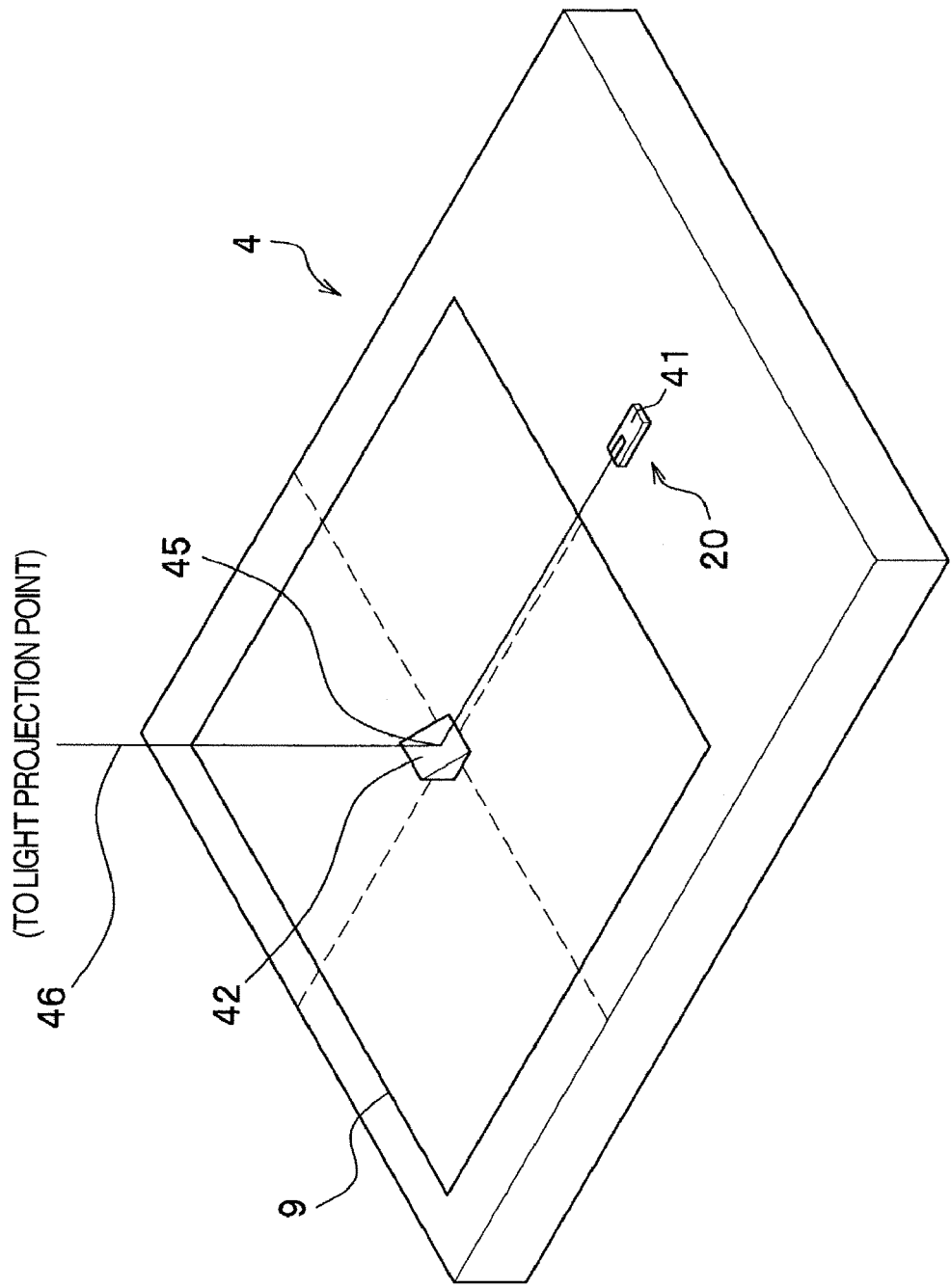
FIG. 13 is a perspective view of a detector of a radiation imaging apparatus (gamma camera) according to a second embodiment of the present invention.

FIG. 13 shows a perspective view of a detector 4 of a radiation imaging apparatus (gamma camera) 1 according to a second embodiment of the present invention. The second embodiment is different in the structure of the light projection means 20 from the variation 3 of the first embodiment (see FIG. 11). The guide advancing mechanism 43 and the turning mechanism 44 are omitted. Further, the mirror 42 is arranged at the center position of the imaging field 9. The first embodiment and its variation 3 allow easy marking. However the gamma cameras 1 thereof become complicated. The second embodiment allows easy marking without major modification to a typical small gamma camera. The laser marker 41 is arranged such that the laser light beam 46 becomes parallel to the imaging field 9. The laser light beam 46 can be emitted perpendicularly to the imaging field 9 by a small mirror 42 attached to the center position of the imaging field 9. If the sensitivity of the detector 4 becomes higher or image processing allows the position of the SLN 32 to be grasped in a few seconds in the future, adjustment of the SLN 32 (target position) to the center position of the imaging field 9 will not become an impediment. The imaging position of the detector 4 is moved such that the SLN 32 is on the center position of the imaging field, and the laser marker 41 is switched on, thereby allowing the light projection mark to be projected on the body surface. A region to be viewed (imaged) is changed also according to the inclination of the detector 4. Accordingly, especially with a hand-held gamma camera 1 that has a small imaging field 9 and the inclination is easily changed, it is difficult to grasp which region on the body surface the imaging field 9 faces. Thus, the laser light beam 46 from the center position of the imaging field 9 and perpendicular thereto indicates which site is presently viewed, thereby allowing more practical use while grasping the light projection position 45 (projected point).

Figure 14:
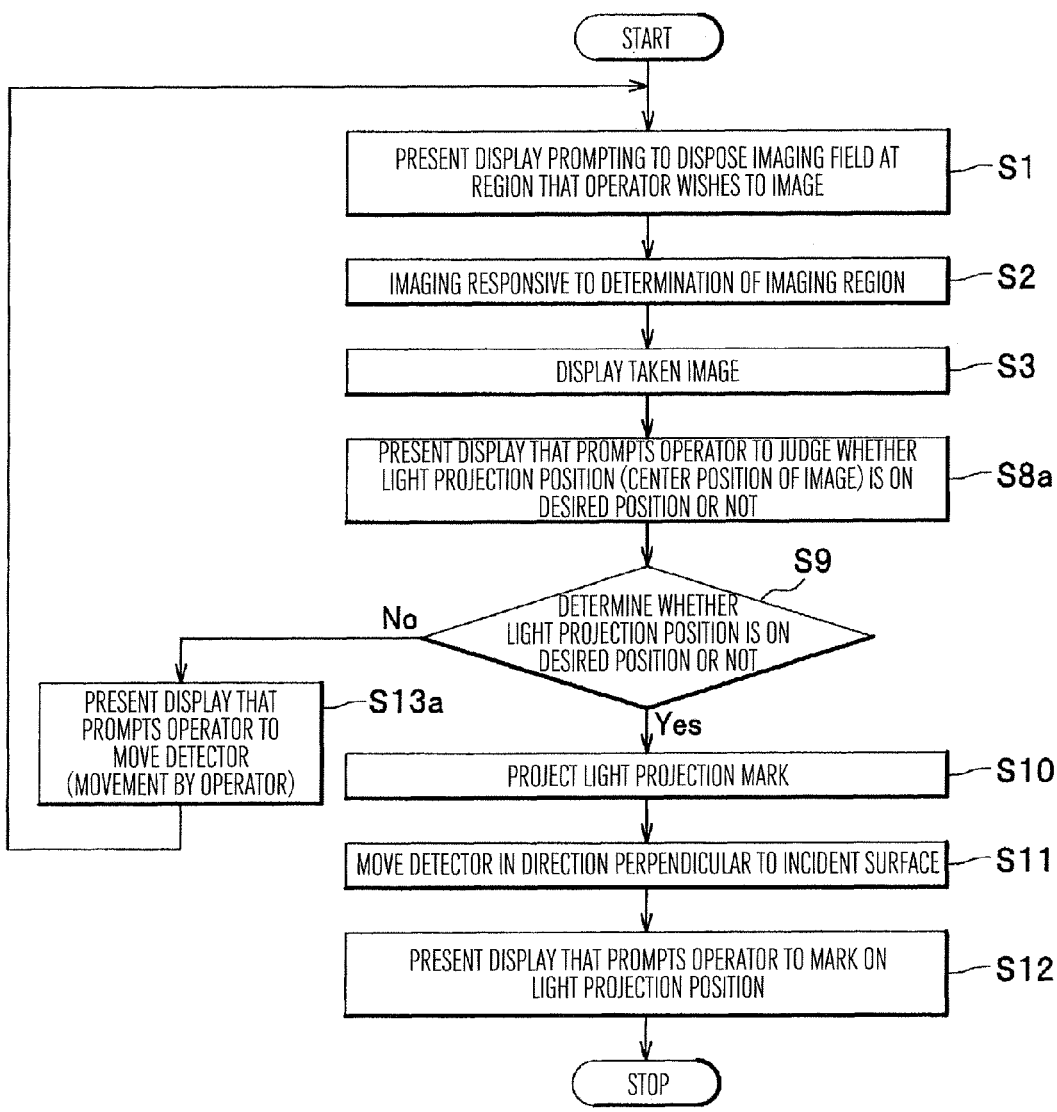
FIG. 14 is a flowchart of a marking method by means of the radiation imaging apparatus (gamma camera) according to the second embodiment of the present invention.

FIG. 14 shows a flowchart of a marking method by means of the radiation imaging apparatus (gamma camera) 1 according to the second embodiment of the present invention. The second embodiment is a type of manual operation, where the detector 4 is manually moved. Accordingly, in comparison with the flowchart of FIG. 12, steps S6 and S7 are omitted. Further, the step S8 is replaced with step S8a. Modified points include that the light projection position is fixed on the center position of the image 7 and immobilized. Further, step S13 is replaced with step S13a. Modified points include that an object to be moved by the operator is changed from the light projection position to the detector 4.

Third Embodiment

Figure 15:
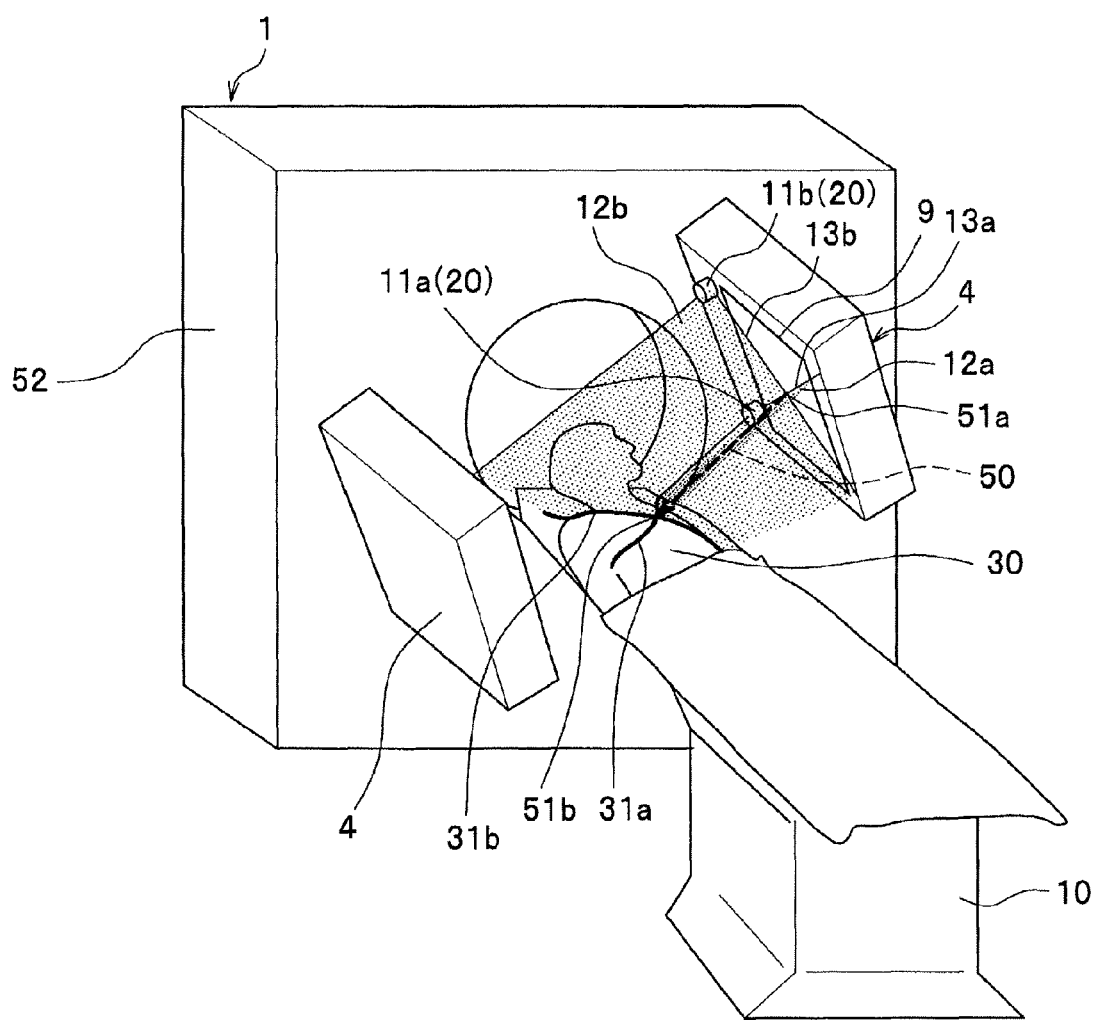
FIG. 15 is a perspective view of a radiation imaging apparatus (SPECT apparatus) according to a third embodiment of the present invention.

FIG. 15 shows a perspective view of a radiation imaging apparatus (SPECT apparatus) 1 according to a third embodiment of the present invention. Since the SPECT apparatus 1 is not portable, it is considered that the above method for use in an operating room is not adopted. In a case of SPECT or gamma camera imaging as an examination, marking for palpation and preliminary confirmation of a target position is very useful, if possible. The SPECT apparatus 1 can obtain a tomogram in addition to a planar image such as by the gamma camera. Attachment of the light projection means 20 to the detector (head) 4 of the SPECT apparatus 1 allows use as with the first embodiment. Further, since a group of obtained tomograms is three-dimensional data, the data can be viewed from any angle.

Figure 16:
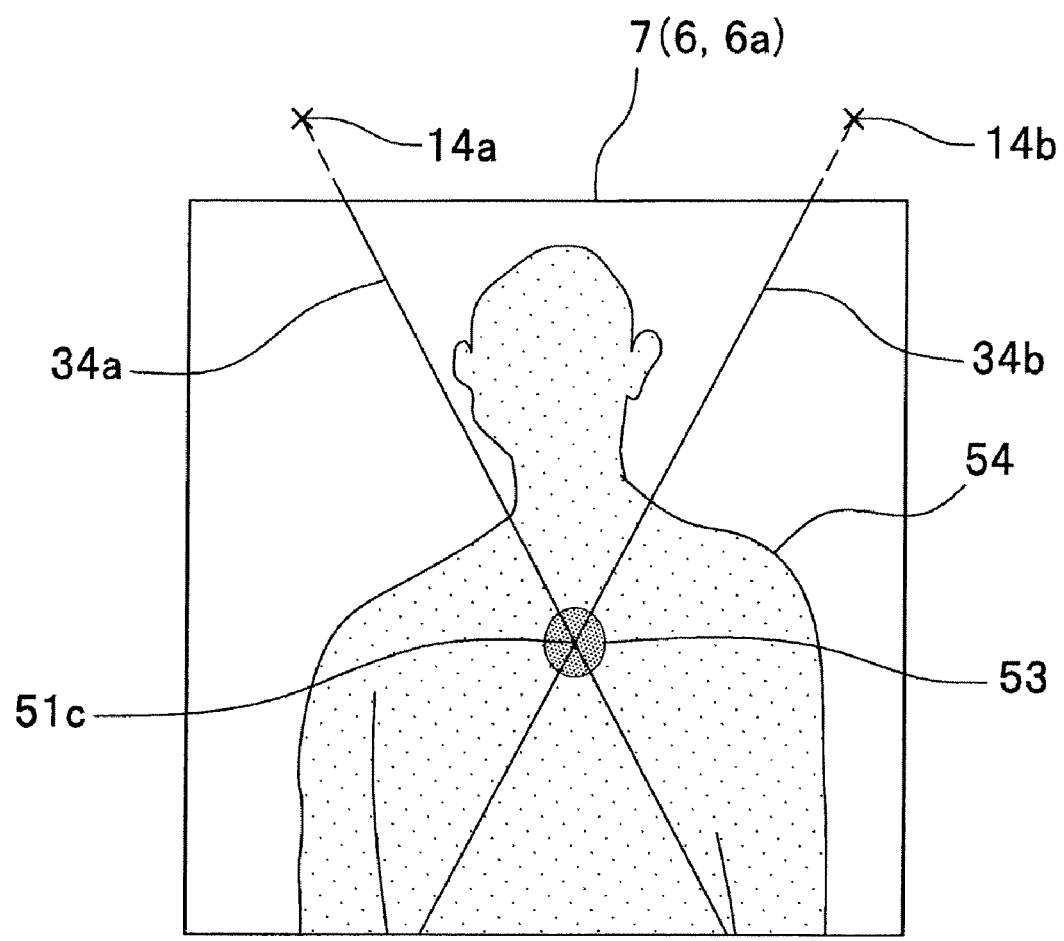
FIG. 16 is an MIP image where a light projection position on an object to be imaged onto which a light projection mark is projected is superimposed on a taken image in a marking method by means of the radiation imaging apparatus (SPECT apparatus).

As shown in FIG. 16, a typically used MIP (maximum intensity projection) image can be obtained as the taken image 7. Internal RI accumulation 53 can be displayed in a manner superimposed on the shape of an object 30 to be imaged viewed from any direction. However, the image of the SPECT apparatus 1 is poor in morphological information such as body contours. In a case without an expensive apparatus including morphological information such as a SPECT/CT, it is useful to display a light projection mark of a tumor and the like on an actual body surface and marking it, for a help of a diagnosis and an operation. Also in a case with a hybrid PET apparatus having a rotating detector 4, such as the SPECT apparatus 1, analogous use is possible. Further, also in a case of a flat panel for imaging an X-ray transparent image and an X-ray CT apparatus, attachment of the light projection means 20 to the detector 4 allows marking on a position on the body surface corresponding to the light projection position on the image 7 in an analogous manner.

The first and second embodiments have been described for medical use. Without limitation thereto, if the techniques are applied to industrial use, for example for an industrial X-ray CT and the like, marking can be performed on a position for processing on a surface based on tomographic information of an object to be imaged.

The above description has been made on the examples. However, the present invention is not limited thereto. It is apparent for a person skilled in the art that various changes and modifications can be made within a scope of the spirit of the present invention and the accompanying claims.

The invention claimed is:

1. A radiation imaging apparatus, comprising:
    a display means which displays an image obtained by imaging an object to be imaged; and
    a light projection means provided in a detector detecting a radiation incident from the object to be imaged; and the light projection means projects a light projection mark on the object to be imaged;
    wherein a light projection position on the object to be imaged onto which the light projection mark is projected is displayed on the image, and the light projection means is operated from an opposite side to an incident surface on which the radiation is incident in the detector in accordance with the light projection position displayed on the image, and the light projection position on the object to be imaged is moved.

2. The radiation imaging apparatus according to claim 1, wherein the detector has a radiation detection means including a plurality of detection elements arranged in a grid pattern for detecting radiation incident from the object to be imaged, and a collimator which limits the radiation incident on the detection element in a direction perpendicular to a surface thereof;
    wherein the display means is provided on the opposite side to the incident surface in the detector and associates a positional relationship between the plurality of the detection elements and a plurality of pixels of the image, and generates and displays the image on the basis of a count value of a detection signal output from the detection element when the radiation is detected; and
    wherein the light projection means arranges the light projection mark in a direction perpendicular to the surface of the collimator from a part of the surface.

3. The radiation imaging apparatus according to claim 2, wherein the light projection means projects the light projection mark as a line of intersection on which two planar flat light beams that are perpendicular to the surface and visually planar intersect with each other; and the light projection position on the image is moved according to a movement of the planar flat light beams.

4. The radiation imaging apparatus according to claim 3, wherein the apparatus calculates projected lines that the light projection lines projected by the planar flat light beams on the object to be imaged are projected on the surface, and displays the projected lines on the image, and thereby displays the light projection position as a point of intersection of the projected lines on the image.

5. The radiation imaging apparatus according to claim 3, wherein the light projection means has a turning mechanism that turns the two planar flat light beams about a turning axis perpendicular to the incident surface.

6. The radiation imaging apparatus according to claim 5, wherein the apparatus calculates projected lines that the light projection lines projected by the planar flat light beams on the object to be imaged are projected on the surface, and displays the projected lines on the image, and thereby displays the light projection position as a point of intersection of the projected lines on the image.

7. The radiation imaging apparatus according to claim 2, wherein the light projection means projects the light projection mark as a line of a light beam perpendicular to the surface, and moves the light projection position on the image according to movement of the light beam.

8. The radiation imaging apparatus according to claim 7, wherein the apparatus calculates a projected point that the light projection point projected by the light beam on the object to be imaged is projected on the surface, and displays the projected point on the image, and thereby displays the light projection position as the light projection point on the image.

9. The radiation imaging apparatus according to claim 2, further comprising a vertical moving means which moves the collimator in a direction perpendicular to the surface.

* * * * *